United States Patent [19]

Kokubo et al.

[11] Patent Number: 4,837,033
[45] Date of Patent: Jun. 6, 1989

[54] METHOD FOR THE PREPARATION OF A COATED SOLID MEDICAMENT

[75] Inventors: Hiroyasu Kokubo; Tohru Chiba, both of Niigata; Fujio Sekigawa, Saitama, all of Japan

[73] Assignee: Shin-Etsu Chemical Co., Ltd., Tokyo, Japan

[21] Appl. No.: 136,864

[22] Filed: Dec. 22, 1987

[51] Int. Cl.⁴ ............................................... A61K 9/16
[52] U.S. Cl. ..................................... 424/494; 424/493; 424/495; 427/213.3
[58] Field of Search .................. 424/493, 494, 495; 427/213.32, 213.3

[56] References Cited

U.S. PATENT DOCUMENTS

| | | | |
|---|---|---|---|
| 3,185,625 | 5/1965 | Brown | 424/494 X |
| 3,477,864 | 11/1969 | Tuji | 424/494 X |
| 3,907,983 | 9/1975 | Seth | 424/494 |
| 3,960,757 | 6/1976 | Morishita et al. | 424/494 X |
| 4,036,948 | 7/1975 | Kitamori et al. | 424/494 X |
| 4,341,563 | 7/1982 | Kurihara et al. | 424/494 X |
| 4,513,019 | 4/1985 | Brancq et al. | 424/494 X |

Primary Examiner—Thurman K. Page
Attorney, Agent, or Firm—Wyatt, Gerber, Burke and Badie

[57] ABSTRACT

Instead of using a uniform aqueous solution of a water-soluble cellulose ether as a coating liquid of solid medicament forms, e.g., granules and tablets, to form a film-forming layer, an aqueous dispersion of a cellulose ether, which is soluble in cold water but insoluble in hot water, is used as a coating liquid at a temperature higher than the solubilization temperature, i.e. the critical point of the solubility behavior, followed by plasticization of the cellulose ether particles with water to cause fusion thereof. The coating liquid is freed from the limitation by the flowability even when the content of the cellulose ether is much higher than in the conventional solution-type coating liquid. In addition to the greatly decreased time taken for forming a coating layer in a desired coating amount, moreover, cellulose ethers having a high degree of polymerization, which cannot be used in the conventional method, can be used so that the resultant film-coating layer is much stronger than otherwise to provide a sustainedly releasing coating layer.

3 Claims, 2 Drawing Sheets

METHOD FOR THE PREPARATION OF A COATED SOLID MEDICAMENT

BACKGROUND OF THE INVENTION

The present invention relates to a method for the preparation of a coated solid medicament form using a cellulose ether as the coating material.

As is well known, most of the solid medicament forms, such as tablets, granules, capsules and the like, in recent years are provided on the surface with a film coating of a polymeric material for the object of protecting the effective ingredients from the influence of the ambient atmosphere as well as imparting an attractive appearance. Various kinds of organic polymers have been used for such a purpose including those soluble in organic solvents and those soluble in water. The use of a polymer soluble in organic solvents is, however, disadvantageous in respect of the expensiveness of the solvent as compared to water as well as the problems of pollution of the environmental atmosphere and adverse influence on the workers' health. Therefore, the technological trend in this matter is toward the use of a water-soluble polymer such as, typically, a water-soluble cellulose ether by directly spraying an aqueous solution of the polymer to the solid medicament forms in a coating machine.

It should be noted that a problem must be solved for the full utilization of water-soluble cellulose ethers as a material for film-coating of solid medicament forms. Namely, the coating solution prepared by dissolving a cellulose ether should have a viscosity not too high to ensure smooth proceeding of the coating procedure. For example, an acceptable coating solution should have a viscosity not much higher than 100 centipoise at the coating temperature when the cellulose ether dissolved therein is a hydroxypropyl methyl cellulose. This limitation in the solution viscosity naturally limits the concentration of the cellulose ether dissolved therein because a solution of higher concentration naturally has a higher viscosity. In this regard, the concentration of the cellulose ether should not exceed 13% by weight or, usually should be in the range from 4 to 12% by weight even when the weight-average degree of polymerization of the hydroxypropyl methyl cellulose is so low as in the range of 65 to 340, of which a 2% by weight aqueous solution has a viscosity of 3 to 15 centipoise at 20° C. Incidentally, the above mentioned weight-average degree of polymerization of the hydroxypropyl methyl cellulose is not an accurate value because no well established method is known for the determination of the average degree of polymerization or average molecular weight of a water-soluble cellulose ether. Accordingly, it is a generally accepted way in the art to define the average degree of polymerization of a water-soluble cellulose ether product not by the actual value thereof but instead by the viscosity of a 2% by weight aqueous solution of the polymer at 20° C., which is referred to as the 2% solution viscosity hereinbelow.

Although no definite standard can be given to the above mentioned 2% solution viscosity which a water-soluble cellulose ether to be used for the film-coating process of solid medicament forms should have, because it is dependent on various factors including the concentration of the cellulose ether in the coating solution, the upper limit of the viscosity of the coating solution, types of the equipments used for the coating process such as coaters and pumps, types of the solid medicament forms to be coated and so on, a water-soluble cellulose ether exhibiting a 2% solution viscosity of several hundreds centipoise or higher can hardly be used as a coating material of solid medicament forms unless the concentration of the coating solution be decreased to less than the desirable range of 5 to 10% by weight to give a viscosity of 1000 centipoise or lower to the coating solution suitable for the coating works. The use of such an unduly diluted coating solution is of course undesirable since a sufficiently thick coating film cannot be obtained on the solid medicament forms by a single procedure of coating to greatly decrease the efficiency of the coating process.

The use of a water-soluble cellulose ether having a low average degree of polymerization is of course undesirable in respect of the low mechanical properties of the coating film formed thereof on the solid medicament forms while the use of a cellulose ether having a high average degree of polymerization is limited for the above mentioned reason. Accordingly, it is eagerly desired to develop an efficient method for providing a film coating on various solid medicament forms by using a high-polymeric water-soluble cellulose ether as the coating material.

SUMMARY OF THE INVENTION

The present invention therefore has an object to provide an efficient method for forming a film coating layer on the surface of solid medicament forms by using a water-soluble cellulose ether having a high degree of polymerization.

The method of the invention for forming a film-coating layer on a solid medicament form using a cellulose ether which is soluble in cold water but insoluble in hot water comprises the steps of:

(a) dispersing particles of the cellulose ether in hot water at a temperature higher than the solubilization temperature of the cellulose ether in water to form an aqueous dispersion;

(b) spraying the aqueous dispersion onto the surface of the solid medicament at a temperature above the solubilization temperature of the cellulose ether form to form a coating layer containing the particles of the cellulose ether thereon;

(c) keeping the coating layer until the particles of the cellulose ether in the coating layer are plastisized with water and fused together to form a uniform coating layer; and (d) drying the coating layer.

DETAILED DESCRIPTION OF THE PREFERRED EMBODIMENTS

Figure 2:
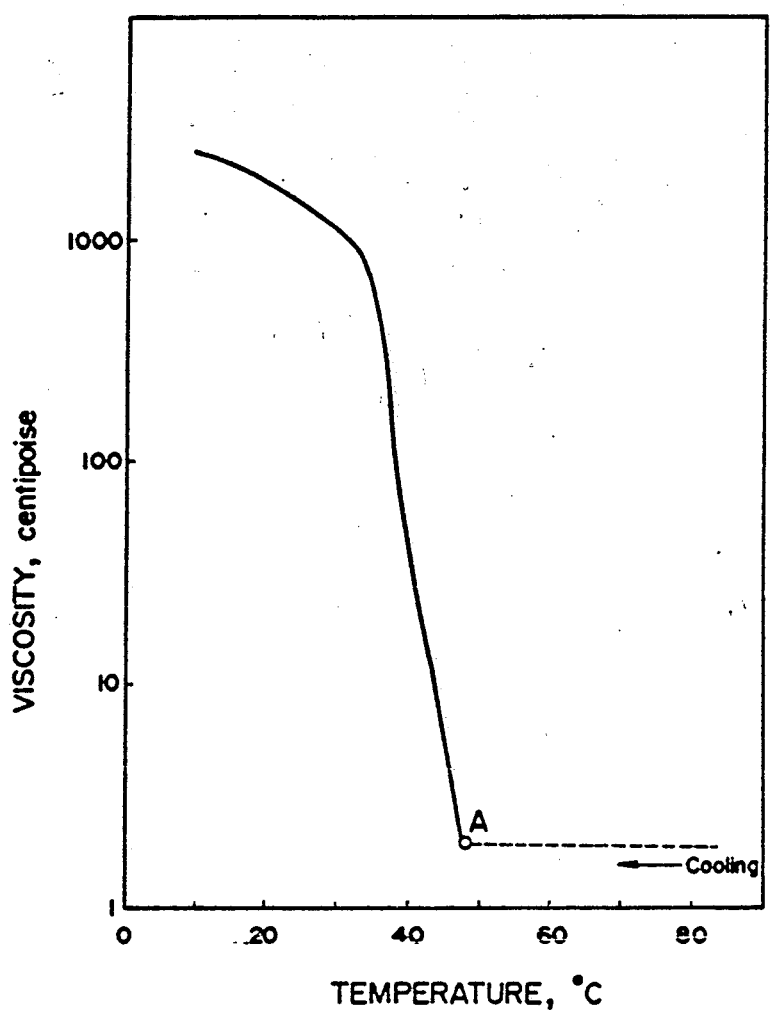
FIG. 2 is a schematic graphic showing to illustrate the solubility behavior of a water-soluble cellulose ether in water in terms of the relationship between viscosity of the aqueous solution and temperature when an aqueous dispersion of the same is cooled.

As is understood from the above given summary of the invention, the most characteristic feature of the inventive method consists in the use of a coating liquid which is not an aqueous solution of a cellulose ether but an aqueous dispersion of particles of a cellulose ether insoluble in hot water. It is known that various cellulose ethers are soluble in cold water but insoluble in hot water at a temperature higher than a critical point, which is dependent on the type of the cellulose ether product. When an aqueous solution of a cellulose ether is gradually heated, the solution is suddenly gelled at a certain critical temperature which is called the gelation temperature or insolubilization temperature. FIG. 2 schematically illustrates the viscosity behavior of an aqueous dispersion-solution of a cellulose ether when an aqueous dispersion of cellulose ether particles dispersed at a temperature higher than the above mentioned insolubilization temperature is gradually cooled. When the temperature of the aqueous dispersion is sufficiently high, the cellulose ether is not dissolved in water at all so that the apparent "viscosity" of the dispersion remains low and almost constant by the decrease in temperature. When the decreasing temperature has reached a point indicated by A in FIG. 2 and is further decreased, the cellulose ether particles are dissolved in water so that the viscosity of the aqueous mixture, which is now an aqueous solution, suddenly begins to increase and the viscosity of the solution continues to increase as the temperature is further decreased. The above mentioned critical point of temperature indicated by A in FIG. 2 is called the solubilization temperature in this invention. Generally, the solubilization temperature of a cellulose ether is somewhat lower than the insolubilization temperature of the same cellulose ether.

The cellulose ether soluble in cold water but insoluble in hot water and suitable for use in the inventive method in respect of the adequate solubilization temperature is exemplified by hydroxypropyl methyl cellulose, methyl cellulose, hydroxypropyl cellulose, hydroxyethyl methyl cellulose and the like, of which hydroxypropyl cellulose and hydroxypropyl methyl cellulose are preferred. The above named methyl cellulose and hydroxypropyl cellulose have a solubilization temperature in the range from 35 to 45° C. Hydroxypropyl methyl cellulose products have different solubilization temperatures depending on the types and, according to Japanese Pharmacopoeia, hydroxypropyl methyl celluloses 2910, 2900 and 2208 have a solubilization temperature in the range of 45 to 55° C., 50 to 60° C. and 60 to 70° C., respectively. Other cellulose ether products having a solubilization temperature higher than the above mentioned ranges are not preferable because preparation of the aqueous dispersion and the coating works therewith must be performed at an unduly high temperature to cause difficulties in the procedure as well as economical disadvantages. Notwithstanding the solubilization temperature close to that of hydroxypropyl cellulose, methyl cellulose having a relatively low solubilization temperature, which is subject to variation by the influence of the content of the methoxyl groups, is less preferable as a coating material of sustainedly releasing solid medicament forms because sometimes no hydrogel of the coating layer is formed on the solid medicament form when the solubilization temperature of a methyl cellulose is not lower than the body temperature while formation of a hydrogel is essential for a sustained release of the effective ingredients from the coated medicament form by the gradual dissolving of the coating layer in the form of a hydro-gel in contact with the digestive fluid. Of course, methyl cellulose is also useful as a coating material when it is combined with another more preferable cellulose ether.

The aqueous dispersion of the cellulose ether to be used as the coating liquid should contain from 5 to 30% by weight of the powdery cellulose ether. When the temperature of the aqueous medium is kept higher than the solubilization temperature of the cellulose ether, the cellulose ether is only very slightly swollen with water and readily dispersed in water by agitation. When agitation is interrupted, the powdery cellulose ether may settle in the medium but readily can be re-dispersed by resuming agitation. When the content of the cellulose ether in the dispersion is too high, the dispersion may have a slurry-like consistency so that difficulties are caused in the coating works, for example, due to clogging of the spray gun nozzles. When the content thereof in the aqueous dispersion is too low, on the other hand, the coating layer formed by a single coating work may have only an unduly small thickness so that the coating procedure must be continued for some length of time to cause an economical disadvantage.

It is of course optional that the aqueous dispersion of the cellulose ether as the coating liquid may contain other additives. For example, water-insoluble powdery materials, such as body pigments and coloring pigments, e.g., talc, finely divided silica powder, titanium dioxide and edible lake pigments, and powders of polymeric materials, can be added although it would be necessary to somewhat decrease the amount of the cellulose ether. The aqueous dispersion may also contain a polymeric material soluble in water irrespective of the temperature with an object to stabilize the aqueous dispersion of the cellulose ether in such a limited amount as to cause no troubles in the spraying work of the coating liquid. Other optional additives to the aqueous dispersion of the cellulose ether include edible dyes, plasticizers such as polyethylene glycol, propylene glycol, glycerin, dibutyl phthalate and the like, flavors such as vanilla, orange oil and the like, and so on.

The particle size distribution of the powdery cellulose ether dispersed in hot water is also an important factor in the inventive method. For example, the powdery cellulose ether should preferably have such a particle size distribution that at least 90% by weight thereof can pass through a #100 screen having a mesh opening of about 149 μm specified in Japanese Pharmacopoeia. When the cellulose ether has a coarser particle size distribution than above, the mutual fusion of the particles in the coating layer formed in the step (b) would be incomplete during the step (c) so that satisfactory coating layers can hardly be obtained.

Various known types of coating machines used for film coating of solid medicament forms can be used without particular limitations in the coating work of tablets, granules, pills, capsules and the like using the aqueous dispersion of a cellulose ether prepared in the above described manner with or without addition of optional additives as the coating liquid. Suitable coating machines include, in addition to conventional pan coaters, the rotating drum-type coating machines such as Accelacota manufactured by Manesty Co., fluidized-bed coating machines such as the machines of the so-called Wurster type developed by Wisconsin University Foundation and the machines manufactured by Glatt Co. and the like. The procedure of the coating works by using these coating machines may also be conventional as in the film-coating procedure in the prior art. The solid medicament forms on which a film coating layer has been formed according to the inventive method can be subjected to polishing, overcoating and other treatments according to need.

The mechanism by which a film coating layer can be formed on the solid medicament forms according to the inventive method involves plasticization of the cellulose ether particles with water which acts as a plasticizer when the temperature of the coated particle is decreased below the solubilization temperature of the cellulose ether. In this regard, use of water as the dispersion medium is advantageous over organic solvents such as alcohol, methylene chloride, acetone and the like by virtue of the large latent heat of vaporization and low velocity of evaporation. It is of course optional that the particles of the cellulose ether are dispersed not in water alone but in a mixture of water and a water-miscible organic solvent. In this case, the organic solvent is first evaporated from the coating layer leaving water which acts as a plasticizer of the cellulose ether particles to cause fusion of the particles into a uniform film-coating layer. It is important that the aqueous dispersion of the cellulose ether should be kept at a temperature higher than the solubilization temperature throughout the coating process to avoid premature plasticization of the cellulose ether particles with water so that suitable heating means must be provided on the pipes for transfer of the aqueous dispersion and other parts of the coating machine according to need.

As compared to the conventional method for film coating of solid medicament forms, the above described inventive method is advantageous due to the absence of limitation laid by the viscosity of the coating liquid so that the content of the cellulose ether in the coating liquid can be much higher than in the conventional coating solution without the problem in the flowability of the coating liquid. The time taken for forming a film-coating layer in a desired coating amount can be much shorter than in the conventional method. In addition, the inventive method is so versatile relative to the molecular weight of the cellulose ether as the coating material so that cellulose ether products of any high degree of polymerization, which can hardly be used in the conventional method, can be used without particular problems. This means that the film-coating layer of the hydrogel formed on the solid medicament forms according to the inventive method can be stronger without being instantaneously destroyed when the coated solid medicament form is orally administered to a patient or applied to the mucous membrane of a patient to give an effect of sustained release of the effective ingredient through the coating layer.

In the following, the method of the present invention is described in more detail by way of examples, in which the terms of "parts" and "%" always refer to "parts by weight" and "% by weight", respectively.

Example 1.

Columnar granules were prepared by extruding a blend composed of 2 parts of vitamin $B_2$, 85 parts of lactose, 10 parts of corn starch and 3 parts of a hydroxypropyl cellulose (HPC-EP, a product by Shin-Etsu Chemical Co.) through an extrusion pelletizer followed by screening through a screen of 0.8 mm diameter openings and drying in a fluidized drying machine at 80° C. for 2 hours. The granules were sorted relative to the columnar length by using a sorter machine.

Separately, an aqueous dispersion of a hydroxypropyl methyl cellulose as a coating liquid was prepared by adding 10 parts of a hydroxypropyl methyl cellulose (60SH-50, a product by Shin-Etsu Chemical Co.) to 90 parts of water kept at 80° C. under agitation. The hydroxypropyl methyl cellulose had a 2% solution viscosity of 50.2 centipoise and such a particle size distribution that about 99% of the particles passed through a #100 screen specified in Japanese Pharmacopoeia. The solubilization temperature of this cellulose ether in an aqueous dispersion was determined by gradually cooling 800 g of the dispersion taken in a beaker of 1 liter capacity at a rate of 1° C./minute under continuous measurement of the viscosity to give a value of 54° C. The thus prepared aqueous dispersion was kept at a temperature of 80° C. or higher until it was fed to the coating machine described below.

A Glatt-type fluidized-bed coating machine (Model WSG-5, manufactured by Ohgawara Seisakusho Co.) was charged with 5 kg of the above prepared granules of vitamin $B_2$ which were coated with the above prepared aqueous dispersion of the cellulose ether as the coating liquid. The coating machine was run under the conditions that the temperature of the air for fluidization was 80° C., temperature of the exhaust was 46 to 50° C. and the feed rate of the coating liquid was 40 g/minute to give a coating amount of 5% based on the uncoated granules. The coating work could be performed in just the same manner as in the conventional procedure except that the coating liquid fed to the coating machine was kept at the elevated temperature mentioned above. It was noted that adhesion of the granules under the coating process took place less frequently than in the conventional procedures to give a yield of at least 90% of the acceptable coated granules.

Example 2.

An aqueous dispersion as a coating liquid was prepared by adding 10 parts of a hydroxypropyl methyl cellulose (60SH-4000, a product by Shin-Etsu Chemical Co.) and 3 parts of talc in 87 parts of hot water under agitation and the dispersion was kept at 80° C. or higher. The cellulose ether had a 2% solution viscosity of 4250 centipoise and had such a particle size distribution that about 99% of the particles could pass the #100 screen. The solubilization temperature of the cellulose ether was 52° C. as determined in the same manner as in Example 1.

The same coating machine was used under the same conditions as in Example 1 to provide a film-coating layer on the columnar granules of vitamin $B_2$ prepared in Example 1 with the above prepared coating liquid to give coated granules in which the coating amount was 5%, 10%, 20% or 40% based on the uncoated granules each in a yield of about 94% of the acceptable coated granules.

Figure 1:
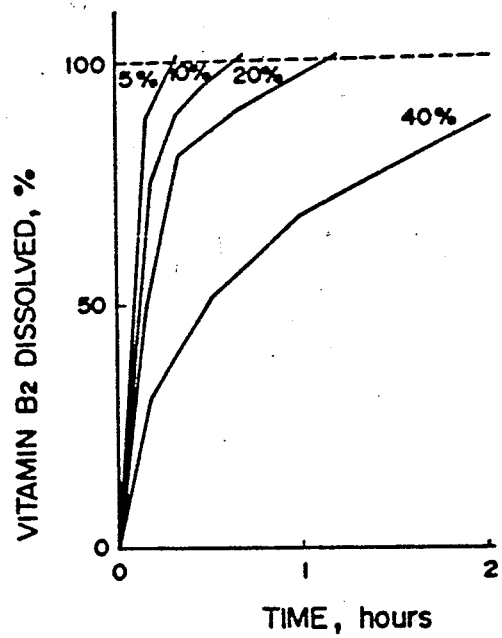
FIG. 1 is a graphic showing of the % dissolution of vitamin $B_2$ into water from the granules containing the same and coated in Example 2 with a film of a water-soluble cellulose in varied coating amounts as a function of time.

The thus obtained coated granules with different coating amounts were subjected to the dissolution test according to the method specified in Japanese Pharmacopoeia by putting a 1 g portion of the coated granules into 900 ml of water at 37° C. as the dissolution medium by the paddle method with the paddle rotating at 100 rpm. The amount of the dissolved vitamin $B_2$ was determined spectrophotometrically by the measurement of the maximum absorption at a wavelength of 444 nm to give the results shown in FIG. 1. As is clear from the figure, the velocity of dissolution of the ingredient was delayed as the coating amount on the coated granules was increased. When the coating amount was 40%, the velocity was so low that a sustained-release coating could be obtained.

Comparative Example 1.

A coating solution was prepared by adding 4 parts of the same hydroxypropyl methyl cellulose as used in Example 1 to 96 parts of hot water at 80° C. with agitation and then cooling the dispersion to 20° C. so that the particles of the cellulose ether were dissolved in water to form a uniform solution.

The same coating procedure as in Example 1 was undertaken except that the aqueous dispersion as the coating liquid introduced into the coating machine was replaced with the above prepared aqueous solution kept at 20° C. and the feed rate of the coating liquid was decreased to 35 g/minute. The results were that the time taken for providing a coating amount of 5% was about 3 times longer than in Example 1 as a consequence of the lower content of the cellulose ether in the coating liquid and the decreased feed rate of the coating liquid to the coating machine. Despite the decreased feed rate of the coating liquid, moreover, adhesion of the granules under the coating procedure took place more frequently than in Example 1 so that the yield of the acceptable coated granules was considerably lower than in Example 1.

What is claimed is:

1. A method for forming a film-coating layer on a solid medicament form with a cellulose ether soluble in cold water but insoluble in hot water which comprises the steps of:
    (a) dispersing particles of the cellulose ether in hot water at a concentration of 5% to 30% by weight at a temperature higher than the solubilization temperature of the cellulose ether in water to form an aqueous dispersion;
    (b) spraying the aqueous dispersion on to the surface of the solid medicament at a temperature above the solubilization temperature of the cellulose ether to form a coating layer containing the particles of the cellulose ether thereon;
    (c) keeping the coating layer until the particles of the cellulose ether in the coating layer are plasticized with water and fused together to form a uniform coating layer; and
    (d) drying the coating layer.

2. The method as claimed in claim 1 wherein the cellulose ether soluble in cold water but insoluble in hot water is selected from the group consisting of hydroxypropyl methyl cellulose, methyl cellulose, hydroxypropyl cellulose and hydroxyethyl methyl cellulose.

3. The method as claimed in claim 1 wherein the particles of the cellulose ether have such a particle size distribution that at least 90% by weight thereof pass through a screen having opening of a diameter of 149 µm.

* * * * *